(12) United States Patent
Dunn

(10) Patent No.: US 6,696,070 B2
(45) Date of Patent: Feb. 24, 2004

(54) STABLE EMULSIONS USEFUL FOR SKIN CARE WIPES

(75) Inventor: Ian Dunn, Albany Creek (AU)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 108 days.

(21) Appl. No.: 09/947,877

(22) Filed: Sep. 6, 2001

(65) Prior Publication Data

US 2002/0123448 A1 Sep. 5, 2002

Related U.S. Application Data

(60) Provisional application No. 60/231,426, filed on Sep. 8, 2000.

(51) Int. Cl.$^7$ ............................ A61K 6/00; A61K 7/00; A01N 25/34
(52) U.S. Cl. ...................... 424/402; 424/400; 424/401; 424/78.03
(58) Field of Search .................................. 424/400, 401, 424/402, 78.03; 514/873

(56) References Cited

U.S. PATENT DOCUMENTS

| | | | | |
|---|---|---|---|---|
| 5,585,104 A | * | 12/1996 | Ha et al. | 424/401 |
| 5,648,083 A | | 7/1997 | Blieszner et al. | 424/402 |
| 5,804,203 A | * | 9/1998 | Hahn et al. | 424/401 |

FOREIGN PATENT DOCUMENTS

| EP | 0 327 326 A1 | 8/1989 |
|---|---|---|
| JP | 03 070707 | 3/1991 |

OTHER PUBLICATIONS

Database Chemical Abstracts Online retrieved from STN Database accession No. 115:189775 XP002199761 (JP 03 070707 A).
"Cationic skin lotions formulated with pemulen® polymeric emulsifier", *Pemulen Polymeric Emulsifiers*, 1995, 1–4.
Clymans, D.R.J. et al., "An alternative to traditional emulsifiers based on stability of multi–phase systems", *Polymeric Emulsifiers*, B F Goodrich Chemical, pp 119–125.
International Search Report for PCT/US 01/27634 datedJul. 3, 2002.

* cited by examiner

*Primary Examiner*—Thurman K. Page
*Assistant Examiner*—S. Howard
(74) *Attorney, Agent, or Firm*—Erin M. Harriman

(57) ABSTRACT

The invention relates to a wet wipe product comprising a substrate and an emulsion. The emulsion comprising: an acrylate/$C_{10}$–$C_{30}$ alkyl acrylate cross polymer emulsifier; salicylic acid; a nonionic surfactant; and a lipophillic component. The nonionic surfactant is selected from the group consisting of (i) a polymeric ether, (ii) a mixture of laurate esters of sorbitol and sorbital anhydrides condensed with ethylene oxide; and (iii) mixtures thereof. The invention also relates to a method for depositing salicylic acid to mammalian skin comprising topically applying the wipe product described above to the skin to be treated. The emulsion according to the invention produces an aesthetically pleasing product, capable of removing non-water proof make-up and able to deliver salicylic acid to the skin and is mild on the skin.

20 Claims, No Drawings

STABLE EMULSIONS USEFUL FOR SKIN CARE WIPES

CLAIM OF PRIORITY

This application claims priority to U.S. Provisional Application No. 60/231,426, filed Sep. 8, 2000, the disclosure of which is hereby incorporated by reference.

FIELD OF THE INVENTION

The invention relates to stable emulsions comprising salicylic acid and acrylates/$C_{10}$–$C_{30}$ alkyl acrylate cross polymers which are used in combination with a substrate to form a wipe product that effectively delivers salicylic acid to the skin while being mild to the skin.

BACKGROUND OF THE INVENTION

Commercial aqueous based facial wipes which contain salicylic acid require either a high level of polyol (such as glycerol or propylene glycol), or ethanol to solubilize the salicylic acid. Unfortunately, formulations with high levels of polyol are perceived by consumers to have poor aesthetic properties (when compared to emulsion type products), while high levels of ethanol can cause irritation to the skin.

Commercial emulsions manufactured for wipe products are preferred to have a viscosity less than 1000 cps to enable impregnation in the conventional manner. Current formulation trends require a complex mixture of surfactants and emulsifiers and emulsification temperatures above 60° C. to incorporate oil phases to produce impregnates at such a viscosity.

Commercial lotions containing salicylic acid and acrylates/$C_{10}$–$C_{30}$ alkyl acrylate cross polymers are stabilized by the use of high quantities of emulsifier (usually emulsifiers which are solid at room temperature) and medium to high viscosity to prevent phase separation. A typical viscosity for such a lotion ranges from about 20,000 to about 100,000 cps.

Emulsions formed by acrylates/$C_{10}$–$C_{30}$ alkyl acrylate cross polymers (in particular those anionic in nature, with a hydrophilic backbone and hydrophobic portions to "lock" the oil in place) are sensitive to salts and soluble cations. The addition of salicylic acid to emulsions containing only acrylates/$C_{10}$–$C_{30}$ alkyl acrylate cross polymers solutions as an emulsifier causes immediate instability and results in separation of the oil and aqueous phase (creaming) or release of the oil phase from the polymer (coalescence) at a pH less than 7.

U.S. Pat. No. 5,648,083 describes personal care compositions including silicones and polymeric emulsifier for providing barrier protection against dermatitis for baby wipes. The compositions do not incorporate cationic species, such as salicylic acid or non-ionic surfactants to modify the surface tension and interact with polymeric emulsifier and oil droplets.

A study released by B F Goodrich, investigating the stability of a cationic surfactant in combination with Pemulen (an acrylates/$C_{10}$–$C_{30}$ alkyl acrylate cross polymer) states that at a pH of 5.5 the maximum concentration of cationic surfactant that remains compatible with the polymer is less than 0.25% by weight, despite increases in polymer concentration from 0.2 to 0.6%. Additional figures show that at higher pH (7.0), stability can be achieved above a viscosity of 1000 mpas. See PEMULEN Polymeric Emulsifiers, "Cationic Skin Lotions Formulated with PEMULEN Polymeric Emulsifiers", 1995.

Polymeric Emulsifiers, "An Alternative to Traditional Emulsifiers based on Stability of Multi-Phase Systems", Daniella R. J. Clymans, Hans M. Brand, B. F. Goodrich Chemical, discusses the use of small chain nonionic surfactants such as Poloxamer 181 (at 0.05–0.2% by weight) or similar products and the use of ethoxylated/propoxylated fatty alcohols to adjust surface properties (such as "quick break effect") and the rheology of PEMULEN emulsions. According to the article these surfactants do not act as emulsifiers, but only reduce the surface tension of the dispersed oily phase at the use level of 0.05–0.2 & by weight.

Accordingly, there remains a need for a stable emulsion including salicylic acid and acrylates/$C_{10}$–$C_{30}$ alkyl acrylate cross polymers.

SUMMARY OF THE INVENTION

The invention relates to a wet wipe product comprising a substrate and an emulsion. The emulsion comprising: an acrylate/$C_{10}$–$C_{30}$ alkyl acrylate cross polymer emulsifier; salicylic acid; a nonionic surfactant; and a lipophillic component. The nonionic surfactant is selected from the group consisting of (i) a polymeric ether, (ii) a mixture of laurate esters of sorbitol and sorbital anhydrides condensed with ethylene oxide; and (iii) mixtures thereof.

The invention also relates to a method for depositing salicylic acid to mammalian skin comprising topically applying the wipe product described above to the skin to be treated.

The emulsion according to the invention produces an aesthetically pleasing product, capable of removing non-water proof make-up and able to deliver salicylic acid to the skin and is mild on the skin.

DETAILED DESCRIPTION

As discussed above, the invention relates to a wet wipe product comprising a substrate and an emulsion, said emulsion comprising:

(a) an acrylate/$C_{10}$–$C_{30}$ alkyl acrylate cross polymer emulsifier;

(b) salicylic acid; and (c) a nonionic surfactant selected from the group consisting of (i) polymeric ether, (ii) a mixture of laurate esters of sorbitol and sorbitol anhydrides condensed with ethylene oxide; and (iii) mixtures thereof.

The acrylate/$C_{10}$–$C_{30}$ alkyl acrylate cross polymer is a white solid powder commercially available from B F Goodrich under the name PEMULEN. It is a high molecular weight cross linked poly(acrylic acid) polymer which contains a hydrophilic back bone and hydrophobic portions which stabilize the oil and lock it in place. The polymer is anionic in nature and can be the only emulsifier used to emulsify the lipophillic components. In a preferred embodiment the acrylates/$C_{10}$–$C_{30}$ alkyl acrylate cross polymer is present in an amount ranging from about 0.05 to about 2.0% by weight, more preferably from about 0.12 to about 0.13% by weight.

The emulsions of the present invention further comprise at least one emulsion stabilizer. Examples of suitable emulsion stabilizers include small chain nonionic surfactants, such as polymeric ethers, including, for example, polyoxyethylene-polyoxypropylene block polymers and nonionic surfactant consisting of a mixture of laurate esters of sorbitol and sorbitol anhydrides, condensed with approximately ethylene oxide. Particularly preferred nonionic surfactants useful as emulsion stabilizers include (1) Poloxamer 124 : A non-ionic surfactant which belongs to the chemical class of polymeric ethers, consisting of a polyoxyethylene, polyoxypropylene block polymer and (2) Polysorbate 20: a nonionic surfactant consisting of a mixture of laurate esters of sorbitol and sorbitol anhydrides, condensed with approximately 20 moles of ethylene oxide.

Although not wishing to be bound by any theory, the proposed mechanism of stabilization is (1) by protection of the hydrophilic backbone by the small chain non-ionic particles to hinder shrinkage and reactions to the salicylic acid; (2) stabilization of the oil droplet at the $C_{10}$–$C_{30}$ alkyl acrylate cross polymer/lipophillic interface by lowering the surface tension and hence nullifying the effects of salicylic acid.; or a combination of both 1 and 2.

In a particularly preferred embodiment, the nonionic surfactant is a mixture of (i) a polyoxyethylene-polyoxypropylene block polymer and (ii) a mixture of laurate esters of sorbitol and sorbital anhydrides condensed with 20 moles of ethylene oxide and is present in amount ranging from about 0.01 to about 10.0% by weight, preferably from about 0.03 to about 0.08% by weight.

The emulsions used in the wipe product of the invention further comprise a cationic active ingredient such as salicylic acid. Preferably, salicylic acid is incorporated for its keratolytic action for the prevention and treatment of comodons and for its slight antibacterial properties. Suitable amounts of salicylic acid range for example, from about 0.05 to about 0.5% by weight, preferably from about 0.05 to about 0.5% by weight.

The emulsions of the invention further comprise a lipophillic component to contribute to the aesthetics of the product. Suitable lipophillic components include as emollients such as $C_{12}$–$C_{15}$ alkyl benzoate; cyclomethicone, dimethicone, and mixtures thereof. The emollients are generally present in an amount ranging from about 0.05 to about 20.0% by weight. In a preferred embodiment, the emulsions according to the invention comprise from about 0.05 to about 0.5% by weight, preferably from about 0.05 to about 0.2% by weight, of cyclomethicone, from about 0.05 to about 0.5% by weight, preferably from about 0.05 to about 0.2% by weight, of dimethicone, and from about 0.05 to about 20.00% by weight, preferably, from about 0.05 to about 1.00% by weight of $C_{12}$–$C_{15}$ alkyl benzoate.

As discussed above, the emulsions used in the wipe product according to the invention are mild to the skin and aesthetically pleasing due to the low concentration of alcohols, such as ethanol, polyols and surfactants. However, the wipe product according may comprise an effective amount of a water-soluble polyol. Water-soluble (which includes water-miscible) polyols are polyols that are able to uniformly dissolve or disperse in water. The water-soluble polyol may serve several purposes in the composition. For example, the polyol may function as a skin moistener, humectant, or emollient The polyol may be used as a solvent for one or more components of the composition.

Water-soluble polyols that are suitable for use herein are taught for example by U.S. Pat. No. 5,648,083, the disclosure of which is hereby incorporated by reference. Suitable water-soluble polyols include water-soluble alkylene polyols and water-soluble analogs of such polyols. Water-soluble analogs of these polyols include water-soluble esters of alkylene polyols. Non-limiting examples of water-soluble polyols suitable for use herein include ethylene glycol, propylene glycol, butylene glycol, diethylene glycols, triethylene glycols, other water-soluble polyethylene glycols, water-soluble soluble polypropylene glycols, hexylene glycol, glycerol, polyoxyethylene sorbitol, 1,2,4-butane triol, 1,2,6-hexane triol, sorbitol and mixtures thereof.

Generally, the polyol or humectant is present in amounts ranging from about 0.5 to about 20% by weight, preferably from about 0.5 to about 5% by weight, most preferably from about 0.5 to about 2% by weight. The compositions of the invention can comprise less than 5% by weight of a polyol and can be free from ethanol.

The emulsions according to the invention may optionally contain an effective amount of any of the preservatives known in the art. Examples of suitable preservatives include phenoxyethanol, methylparaben, ethylparaben, propylparaben, butylparaben, isobutylparaben, and mixtures thereof. A particularly preferred preservative is PHENONIP which is a mixture of phenoxyethanol, methylparaben, ethylparaben, propylparaben, and butylparaben commercially available from Nipa Laboratories, Inc.

Another optional component useful in the emulsions according to the invention is any of the anti-irritants known in the art. The anti-irritant should be present in an amount effective to provide anti-irritation properties to the compositions. An example of a suitable anti-irritant is allantoin which is generally present at from about 0.05 to about 2.00% by weight, more preferably, from about 0.05 to about 0.5% by weight.

The inclusion of small chain non-ionic surfactants at low levels, stabilizes the polymeric emulsifier at a pH less than 7 for incorporation into fabric. In one embodiment, the pH of the emulsion of the invention can range from about 4.0 to about 5.5. The pH can be adjusted by adding one or more pH-adjusting agents in an amount effective to provide such pH values (herein alternatively referred to as "an effective amount"). Agents that may be used to adjust the pH of the compositions herein include organic and inorganic acids and bases. An example of a suitable base is sodium hydroxide. The viscosity is less than 1000 cps which allows for impregnation into fabric in the conventional manner.

Exemplary preferred compositions of the present invention include the ingredients and ranges of concentrations set forth in Table 1 below:

TABLE 1

| Item No. | CTFA Name | Preferred Range | Range |
|---|---|---|---|
| 1. | Acrylates/C10–30 Alkyl Acrylate Cross polymer | 0.120–0.13% w/w | 0.05–2.00% w/w |
| 2. | Salicylic Acid | 0.05–0.5% w/w | 0.05–0.5% w/w |
| 3. | Poloxamer 124 | 0.03–0.08 | 0.01–10.00% |
| 4. | Polysorbate 20 | 0.03–0.08 | 0.01–10.00% |
| 5. | Cyclomethicone | 0.05–0.2% w/w | 0.05–0.5% w/w |
| 6. | Dimethicone | 0.05–0.1% w/w | 0.05–0.5% w/w |
| 7. | C12–15 Alkyl Benzoate | 0.05–1.00% w/w | 0.05–20.00% w/w |
| 8. | Fragrance | 0.01–1.00% w/w | 0.0–1.00% w/w |
| 9. | Butylene Glycol | 0.5–2.00% w/w | 0.5–10.0% w/w |
| 10. | Propylene Glycol | 0.5–2.00% w/w | 0.5–10.0% w/w |
| 11. | Phenoxyethanol Methylparaben, Propylparaben, Butylparaben, Isobutyl Paraben Ethyl Paraben | 1.000% w/w | 1.000% w/w |
| 12. | Sodium Hydroxide | 0.3–0.6% w/w | 0.2–1.0% w/w |
| 13. | Allantoin | 0.05–0.5% w/w | 0.05–2.00% w/w |
| 14. | Water | To 100% w/w | To 100% w/w |

The compositions may be prepared by oil-in-water emulsion techniques such as are known or become known in the art, such as taught, for example, by U.S. Pat. No. 5,648,083, the disclosure of which is hereby incorporated by reference. In general, the process involves the steps of preparing a mixture of the ingredients of the composition and subjecting the mixture to conditions to cause the formation of a homogeneous and stable oil-in-water emulsion (a suspension of the silicone oil in the water and water-soluble materials is formed). Homogeneity is indicated by a composition which is substantially smooth, lump-free and uniform in appearance. A stable emulsion remains homogeneous over a given period which is determined by the required shelf life of the composition.

As used herein, "wipe product" means a substrate and a composition of the present invention which are pre-combined for later use. Suitable wipe substrates include those known in the art such as nonwovens, films, foams, sponges, and the like, as taught for example by U.S. Pat. Nos. 5,648,083, 3,905,863, 3,974,025, and 4,191,609. Each of these references are incorporated herein by reference in their entirety. Preferred wipe substrates comprise a porous material which is capable of holding the composition within the pores of the substrate.

Techniques for combining wipe substrates with a cleansing or treating composition, and for their packaging are well known in the art and are applicable to the present invention. In general, the wipe substrate is combined with the composition by one or more techniques involving coating, immersing, dipping, spraying, extruding, and the like. In general, the wipes are combined with an amount of the composition sufficient to provide good effective cleansing.

The use of the polymeric emulsification system allows for cold process manufacture, which in effect, decreases batch cycle time, decreases equipment requirements of manufacturer (heated vessels not required) and hence decreases the costs to manufacture.

The use of the polymeric emulsifier has also produced an aesthetically pleasing product which delivers salicylic acid to the skin, yet has been proven by clinical testing to be mild on skin. Accordingly, in another embodiment the invention relates to a method for depositing salicylic acid to mammalian skin comprising topically applying a wipe product comprising an emulsion comprising: an acrylate/$C_{10}$–$C_{30}$ alkyl acrylate cross polymer emulsifier; salicylic acid; a nonionic surfactant; and a lipophillic component. The nonionic surfactant is selected from the group consisting of (i) a polymeric ether, (ii) a mixture of laurate esters of sorbitol and sorbital anhydrides condensed with ethylene oxide; and (iii) mixtures thereof. The emulsion can be used as a "leave on" composition or rinsed from the skin with water.

EXAMPLES

The advantages of the invention and specific embodiments of the emulsions prepared in accordance with the present invention are illustrated by the following examples. It will be understood, however, that the invention is not confined to the specific limitations set forth in the individual examples, but rather defined within the scope of the appended claims.

Example 1

An emulsion according to the invention was prepared according to the following process:
1. Sodium Hydroxide Preparation
1.0 Prepare sufficient 10% Sodium Hydroxide
1.1 Prepare sufficient 30% Sodium Hydroxide
2. Phase A (Bulk Phase)
2.0 Add purified water (50% of total) to the main mixing vessel Start the propeller type mixer
2.1 Slowly add Acrylates/C10–C30 Alkyl Acrylate Cross Polymer into the water. Mix until dispersed
2.3 Slowly add, Cylcomethicone, Dimethicone and C12–C15 Alkyl Benzoate with mixing to the vat
2.4 Pre Neutralize with 10% Sodium Hydroxide
2.5 Add Polysorbate 20 and Poloxamer 124 with gently mixing. Pre-mix Allantoin with water, followed by Fragrance and add with mixing. When dispersed, transfer to a Homogenization tank. Homogenize the solution for 5–10 minutes. Return the homogenized solution to the main mixing vessel
2.6 Add the Phenoxyethanol, Methylparaben, Propylparaben, Ethylparaben, Isobutylparaben and Butylparaben with mixing.
2.7 Neutralize to a pH of 5.2–5.5 with quantity sufficient 10% Sodium Hydroxide Solution.

3. Phase B (Salicylic Acid Pre-Mix)
3.0 In a separate vessel, mix Butylene Glycol, Propylene Glycol, Salicylic Acid and Sodium 3.1 hydroxide 30% solution until a uniform solution is achieved.
3.2 Add Water (50% w/w of total). While mixing, adjust pH to a value of 5.0–5.5 with quantity sufficient 30% Sodium Hydroxide Solution.
4. Phasing
4.0 Slowly add the Phase B (Salicylic Acid Pre-Mix) to Phase A (Bulk Phase) with gentle mixing by a propeller mixer over a 10–20 minute period.
4.1 Check pH and Adjust to 4.8–5.2 with the 10% Sodium Hydroxide Solution.
4.2 Continue mixing for a further 15 minutes, recheck pH and adjust if required.

The formulation of the emulsion is set forth in Table 2 below:

TABLE 2

| Component CTFA/ Technical Name | Function | % (w/w) |
| --- | --- | --- |
| C10–C30 Alkyl acrylate cross polymer | Emulsifier | 0.125 |
| Salicylic Acid | Keratolytic Agent | 0.500 |
| Poloxamer 124 | Nonionic Surfactant | 0.031 |
| Polysorbate 20 | Nonionic Surfactant | 0.050 |
| Cyclomethicone | Emollient | 0.200 |
| Dimethicone | Emollient | 0.100 |
| C12–15 Alkyl benzoate | Emollient | 0.500 |
| Fragrance | Perfume | 0.060 |
| Butylene glycol | Humectant | 1.00 |
| Propylene Glycol | Humectant | 2.00 |
| PHENONIP* | Preservative | 1.00 |
| Sodium Hydroxide | Neutralizer | 0.425 |
| Allantoin | Anti-irritant | 0.200 |
| Water | Vehicle | q.s. |

*PHENONIP is mixture of phenoxyethanol, methylparaben, ethylparaben, propylparaben, and butylparaben commercially available from Nipa Laboratories, Inc.

Example 2

Salicylic Acid Deposition

The composition of Example 1 impregnated on a non-woven substrate. Two panelists (A and B) were asked to use three cleansing wipes consecutively on one side of the nose and naso-labial area. The side of the nose tested was assigned randomly. The area was then allowed to air-dry for at least 5 minutes. After, the area was rinsed off with running water for 10 seconds and allowed to air-dry for another 5 minutes.

The area was then traced on a microscope slide cleaned previously with methanol-water (50%/50%) and isoproanol. A small amount of cyanoacrylate glue was applied directly on the nose area and was allowed to remain for 1½ minutes. Afterwards, glue was also applied on the area marked on the slide. The slide was then firmly pressed against the nose area (with the dried glue) and was held in place for another 1½ minutes, after which the slide was gently peeled off from the nose. The dried glue on the slide contained debris from the skin pores (i.e., sebum plugs).

The sebum plugs were scraped from each slide into individual small test tubes. Little or no cyanoacrylate glue was included in the sample. The samples were then dissolved in acetonitrile:3% acetic acid (60:40).

Salicylic acid was detected by HPLC analysis (Mobile phase=acetonitrile:3% acetic acid (60:40); flow rate=1 ml/min; injection volume=20 µL; detector wavelength=305 nm; run time=5 minutes; column=C8.) The sebum plugs of Panelist A showed 1.5 μg salicylic acid deposition and those of Panelist B showed 2.4 μg salicylic acid deposition. Accordingly, the emulsions according to the invention are capable of depositing salicylic acid into skin pores even with rinsing.

Example 4

Stability Study of Emulsions According to the Invention

In this Example, the composition of Example 1 was modified as set forth below and the shelf life recorded in Table 3.

TABLE 3

| % w/w Poloxamer 124 | % w/w Polysorbate 20 | % w/w Lipophillic Phase | % w/w Acrylates/ C10–30 Alkyl Acrylate Cross Polymer | Shelf-Life (remained homogeneous) |
|---|---|---|---|---|
| 0.0 | 0.0 | 2.00 | 0.125 | 0 Hours |
| 0.0 | 0.0 | 2.00 | 0.150 | 0 Hours |
| 0.0 | 0.63 | 2.00 | 0.125 | 24 Hours |
| 0.03 | 0.03 | 2.85 | 0.150 | 24 Hours |
| 0.08 | 0.08 | 2.00 | 0.125 | 48 Hours |
| 0.03 | 0.03 | 2.00 | 0.125 | 48 Hours |
| 0.03 | 0.05 | 2.00 | 0.125 | 72 Hours |
| 0.03 | 0.05 | 0.80 | 0.125 | 72 Hours |

What is claimed is:

1. A wet wipe product comprising a substrate and a stable emulsion, said emulsion comprising:
   (a) an acrylate/$C_{10}$–$C_{30}$ alkyl acrylate cross polymer emulsifier;
   (b) salicylic acid; and
   (c) a nonionic surfactant selected from the group consisting of (i) a polymeric ether, (ii) a mixture of laurate esters of sorbitol and sorbital anhydrides condensed with ethylene oxide; and (iii) mixtures thereof,
   wherein said emulsion has a viscosity of less than 1000 cps.

2. The wipe product according to claim 1, wherein the nonionic surfactant is a mixture of (i) a polyoxyethylene-polyoxypropylene block polymer and (ii) a mixture of laurate esters of sorbitol and sorbital anhydrides condensed with 20 moles of ethylene oxide.

3. The wipe product according to claim 1, comprising
   (a) from about 0.05 to about 2.00% by weight of said acrylate/$C_{10}$–$C_{30}$ alkyl acrylate cross polymer emulsifier;
   (b) from about 0.05 to about 0.50% by weight said salicylic acid; and
   (c) from about 0.1 to about 10% by weight of said nonionic surfactant.

4. The wipe product according to claim 2, comprising
   (a) from about 0.12 to about 0.13% by weight of of said acrylate/$C_{10}$–$C_{30}$ alkyl acrylate cross polymer emulsifier;
   (b) from about 0.05 to about 0.50% by weight said salicylic acid; and
   (c) from about 0.03 to about 0.08% by weight of a polyoxyethylene-polyoxypropylene block polymer and from about 0.03 to about 0.08% of a mixture of laurate esters of sorbitol and sorbital anhydrides condensed with 20 moles of ethylene oxide.

5. The wipe product according to claim 1, further comprising an effective amount of at least one emollient selected from the group consisting of $C_{12}$–$C_{15}$ alkyl benzoate; cyclomethicone, dimethicone, and mixtures thereof.

6. The wipe product according to claim 1, further comprising an effective amount of at least one humectant selected from the group consisting of butylene glycol, propylene glycol, ethylene glycol, hexylene glycol, diethylene glycols, triethylene glycols, water soluble polyethylene glycols, water soluble polypropylene glycols, glycerol, polyoxyethylene sorbitol, 1,2,4-butane triol, 1,2,6-hexane triol, sorbitol and mixtures thereof.

7. The wipe product according claim 1, further comprising an effective amount of a preservative selected from the group consisting of phenoxyethanol, methylparaben, ethylparaben, propylparaben, butylparaben, isobutylparaben, and mixtures thereof.

8. The wipe product according to claim 1, wherein said emulsion has a viscosity of less than about 1000 cps.

9. The wipe product according to claim 1, wherein said emulsion has a pH of from about 4.0 to about 5.5.

10. The wipe product according to claim 1, further comprising an effective amount of at least one anti-irritant.

11. The wipe product according to claim 10, wherein said anti-irritant is allantoin.

12. The wet wipe product according to claim 1, wherein said emulsion is free from ethanol.

13. The wet wipe product according to claim 1, wherein said emulsion comprises less than 5% of a polyol.

14. The wipe product according to claim 1, wherein said emulsion is prepared by cold process emulsification.

15. A method for depositing salicylic acid to mammalian skin comprising topically applying the wipe product according to claim 1 to said skin.

16. The method according to claim 15, further comprising the step of rinsing with water the area of the skin treated.

17. A wet wipe product comprising a substrate and an emulsion, said emulsion comprising:
   (a) from about 0.05 to about 2.00% by weight of an acrylate/$C_{10}$–$C_{30}$ alkyl acrylate cross polymer emulsifier;
   (b) from about 0.05 to about 0.50% by weight salicylic acid;
   (c) from about 0.01 to about 10% of a polyoxyethylene-polyoxypropylene block polymer;
   (d) from about 0.01 to about 10% of a mixture of laurate esters of sorbitol and sorbital anhydrides condensed with 20 moles of ethylene oxide;
   (e) from about 0.05 to about 20% by weight of at least one emollient selected from the group consisting of $C_{12}$–$C_{15}$ alkyl benzoate; cyclomethicone, dimethicone, and mixtures thereof; and
   (f) from about 0.5 to about 20% of at least one humectant selected from the group consisting of butylene glycol, propylene glycol, and mixtures thereof.

18. The wipe product according to claim 17, wherein said emulsion has a pH ranging from about 4.0 to about 5.5 and a viscosity of less than about 1000 cps.

19. The wipe product according to claim 17, further comprising from about 0.05 to about 2.00% by weight of at least one anti-irritant.

20. The wipe product according to claim 19, wherein the anti-irritant is allantoin.

* * * * *